US011324880B2

(12) United States Patent
Garibaldi et al.

(10) Patent No.: US 11,324,880 B2
(45) Date of Patent: May 10, 2022

(54) INFUSION MONITORING SYSTEM

(71) Applicant: CareFusion 303, Inc., San Diego, CA (US)

(72) Inventors: Federico Garibaldi, San Diego, CA (US); Yared Akalou, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 17/400,779

(22) Filed: Aug. 12, 2021

(65) Prior Publication Data

US 2021/0369955 A1 Dec. 2, 2021

Related U.S. Application Data

(63) Continuation of application No. 16/842,119, filed on Apr. 7, 2020, which is a continuation of application (Continued)

(51) Int. Cl.
*A61M 5/142* (2006.01)
*G16H 40/63* (2018.01)
(Continued)

(52) U.S. Cl.
CPC ....... *A61M 5/14228* (2013.01); *G06F 3/0481* (2013.01); *G06F 3/0484* (2013.01); *G06F 16/447* (2019.01); *G16H 20/17* (2018.01); *G16H 40/63* (2018.01); *G16H 40/67* (2018.01); *A61M 2005/14208* (2013.01); *A61M 2205/3553* (2013.01); *A61M 2205/3584* (2013.01); *A61M 2205/3592* (2013.01); (Continued)

(58) Field of Classification Search
CPC .... G06F 3/0484; G06F 16/447; G06F 3/0481; A61M 2005/14208; A61M 2205/3553; A61M 2205/502
See application file for complete search history.

(56) References Cited

U.S. PATENT DOCUMENTS 5,713,856 A 2/1998 Eggers et al.
5,781,442 A 7/1998 Engleson et al.
(Continued)

FOREIGN PATENT DOCUMENTS

CN 1561241 A 1/2005
CN 101360453 A 2/2009
(Continued)

*Primary Examiner* — Mandrita Brahmachari
(74) *Attorney, Agent, or Firm* — Mintz, Levin, Cohn, Ferris, Glovsky and Popeo, P.C.

(57) ABSTRACT

An infusion management and monitoring system comprises an infusion pump and instructions executable by a processor to cause a remote device separate from and in communication with the infusion pump to receive data for a medication to be administered to a patient via the infusion pump within a healthcare environment; receive from the infusion pump data for administration of the medication to the patient; determine a status of the administration of the medication based on at least one of the data for the medication or the data for the administration of the medication; and transmit the status to a mobile communication device within the healthcare environment.

30 Claims, 6 Drawing Sheets

Related U.S. Application Data

No. 14/835,964, filed on Aug. 26, 2015, now Pat. No. 10,625,015, which is a continuation of application No. 13/802,339, filed on Mar. 13, 2013, now Pat. No. 9,177,108.

(51) Int. Cl.
| | | |
|---|---|---|
| *G16H 20/17* | (2018.01) | |
| *G16H 40/67* | (2018.01) | |
| *G06F 16/44* | (2019.01) | |
| *G06F 3/0481* | (2022.01) | |
| *G06F 3/0484* | (2022.01) | |

(52) U.S. Cl.
CPC . *A61M 2205/502* (2013.01); *A61M 2205/505* (2013.01); *A61M 2205/507* (2013.01)

(56) References Cited

U.S. PATENT DOCUMENTS

| | | | |
|---|---|---|---|
| 7,945,452 | B2 | 5/2011 | Fathallah et al. |
| 7,999,810 | B1 | 8/2011 | Boice et al. |
| 8,078,983 | B2 | 12/2011 | Davis et al. |
| 8,435,206 | B2 | 5/2013 | Evans et al. |
| 8,553,039 | B1 | 10/2013 | Boice et al. |
| 2003/0009244 | A1* | 1/2003 | Engleson .............. G16H 20/17 700/86 |
| 2003/0140928 | A1 | 7/2003 | Bui et al. |
| 2005/0010447 | A1 | 1/2005 | Miyasaka et al. |
| 2006/0229557 | A1 | 10/2006 | Fathallah et al. |
| 2008/0086333 | A1* | 4/2008 | Hertel .................. G06Q 10/10 705/2 |
| 2010/0121654 | A1 | 5/2010 | Portnoy et al. |
| 2011/0029324 | A1 | 2/2011 | Kondo et al. |
| 2011/0072379 | A1 | 3/2011 | Gannon et al. |
| 2012/0029941 | A1 | 2/2012 | Malave et al. |
| 2012/0310152 | A1 | 12/2012 | Wehba et al. |
| 2012/0323090 | A1 | 12/2012 | Bechtel et al. |
| 2013/0047113 | A1 | 2/2013 | Hume et al. |
| 2013/0055106 | A1 | 2/2013 | Tarneberg et al. |
| 2013/0148532 | A1 | 6/2013 | Poon et al. |
| 2013/0152005 | A1 | 6/2013 | McLaren et al. |
| 2014/0068487 | A1 | 3/2014 | Steiger et al. |
| 2014/0276560 | A1 | 9/2014 | Sehgal et al. |
| 2016/0103960 | A1 | 4/2016 | Hume et al. |

FOREIGN PATENT DOCUMENTS

| | | |
|---|---|---|
| CN | 102387217 A | 3/2012 |
| JP | 2000042103 A | 2/2000 |
| JP | 2005501340 A | 1/2005 |
| JP | 2008535634 A | 9/2008 |
| JP | 2009151806 A | 7/2009 |
| JP | 2012128554 A | 7/2012 |
| WO | WO-03/019402 A1 | 3/2003 |
| WO | WO-2005/086819 A2 | 9/2005 |
| WO | WO-2006/110851 A2 | 10/2006 |

\* cited by examiner

INFUSION MONITORING SYSTEM

TECHNICAL FIELD

This application is a continuation of U.S. patent application Ser. No. 16/842,119 filed Apr. 7, 2020, which is a continuation of U.S. patent application Ser. No. 14/835,964 filed Aug. 26, 2015 and now issued as U.S. Pat. No. 10,625,015, which is a continuation of U.S. patent application Ser. No. 13/802,339 filed Mar. 13, 2013 and now issued as U.S. Pat. No. 9,177,108, the contents of which are herein incorporated by reference in their entirety.

BACKGROUND

Patients undergoing complex or prolonged medical care often receive multiple medications that are infused via various mechanisms including, for example, intravenous (IV) therapies, patient controlled analgesia, and syringe therapies. As the number of infusions for a particular patient, so does the complexity from a caregiver perspective. The caregiver needs to know when and what new medications are due, what specimens have been collected, when lab results are ready, the indications from the lab results, and the like. Furthermore, with large number of infusions, difficulties can also arise with regard to complete and accurate charge capture.

SUMMARY

In one aspect, data is received that characterizes infusions administered to a patient among each of a plurality of infusion channels. Thereafter, a plurality of infusion events and respective event times are identified based on the received data. A temporal view of the infusion events can then be displayed in a graphical user interface and/or the temporal view of the infusion events can form part of a report. The temporal view segregates each channel into a separate swim lane with each swim lane visualizing infusion events for the corresponding channel at the respective event times.

The events can be of event types such as infusion start time, infusion end time, infusion paused, medication container change. Each event type can have a different visual indicator in the graphical user interface. There can be pluralities of infusion types and, optionally, each infusion type can have a different visual indicator in the graphical user interface.

At least a portion of the received data can be received, via a computer network, from at least one infusion module that automatically infuses medication to the patient. The received data can be received in real-time as the data is generated by at least one infusion module. The received data can include historical data or lab data. In other variations, the received data includes a combination of at least two of: real-time data, historical data, and lab data.

A rules engine and a plurality of pre-defined infusion event rules can be used to determine whether the received data comprises at least one infusion event.

In some variations, the graphical user interface can also display, concurrent with the temporal view of the infusion events, a view characterizing at least one manually administered medication.

The infusion events visualized in each swim lane can include bars extending from a starting time point at which an infusion begins on the corresponding channel until an ending time point at which the infusion on the channel ends.

The data generated for the graphical user interface can be loaded into memory, transmitted to a remote computing system and/or stored in memory or other persistent storage.

Computer program products are also described that comprise non-transitory computer readable media storing instructions, which when executed one or more data processor of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The subject matter described herein provides many advantages. For example, the graphical user interfaces as described and illustrated herein allow caregivers and/or pharmacists to readily identify what infusions have been provided over which infusion channels and over what time periods. Furthermore, the graphical user interfaces as described and illustrated herein are advantageous in that they enable billing specialists to have an accurate and complete view of various infusions given to a patient so that they may be coded and correctly charged.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
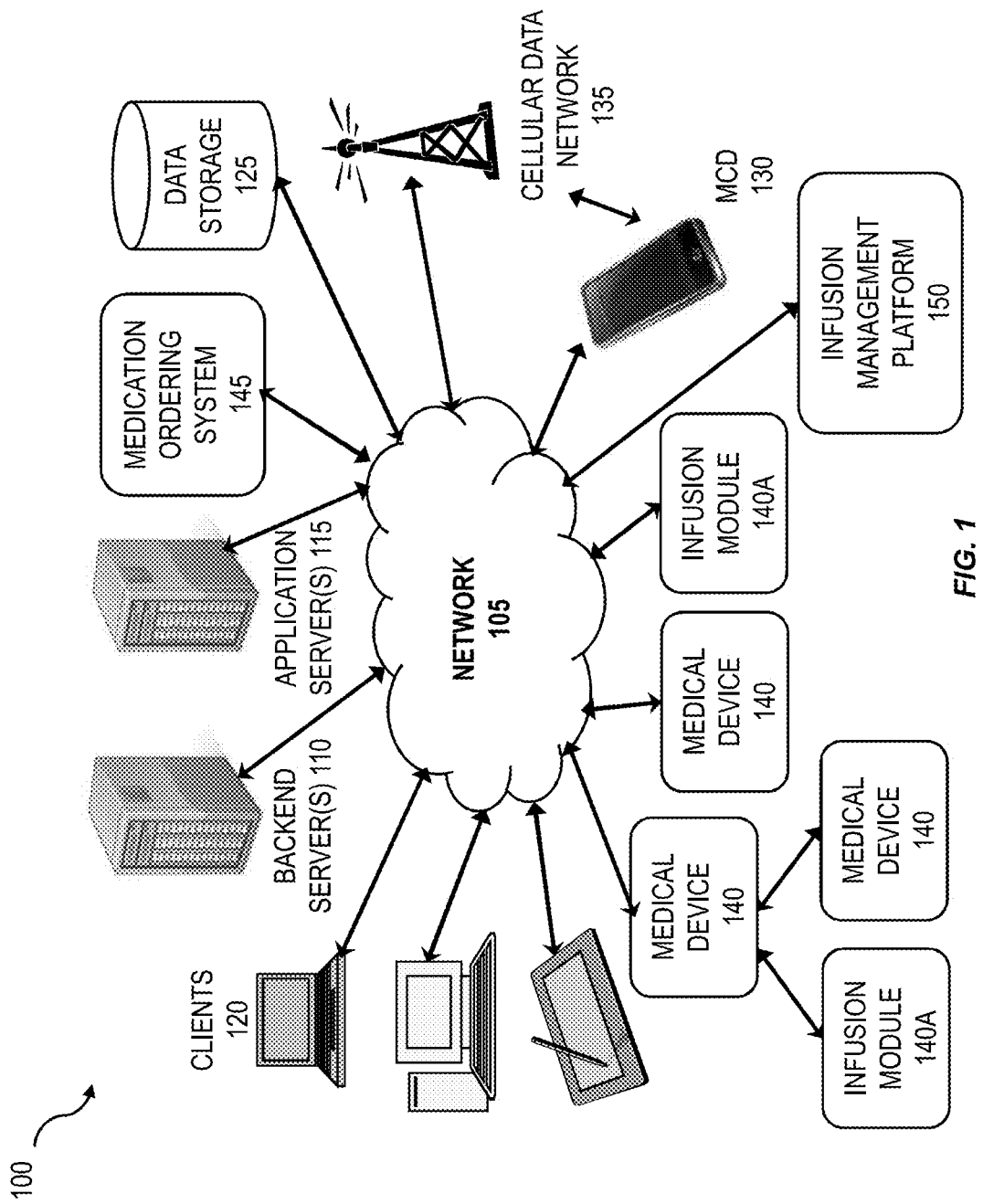
FIG. 1 is a system diagram illustrating a computing landscape within a healthcare environment.

FIG. 1 is a system diagram illustrating a computing landscape 100 within a healthcare environment such as a hospital. Various devices and systems, both local to the healthcare environment and remote from the healthcare environment, can interact via at least one computing network 105. This computing network 105 can provide any form or medium of digital communication connectivity (i.e., wired or wireless) amongst the various devices and systems. Examples of communication networks include a local area network ("LAN"), a wide area network ("WAN"), and the Internet. In some cases, one or more of the various devices and systems can interact directly via peer-to-peer coupling (either via a hardwired connection or via a wireless protocol such as Bluetooth or WiFi). In addition, in some variations, one or more of the devices and systems communicate via a cellular data network.

In particular, aspects of the computing landscape 100 can be implemented in a computing system that includes a back-end component (e.g., as a data server 110), or that includes a middleware component (e.g., an application server 115), or that includes a front-end component (e.g., a client computer 120 having a graphical user interface or a Web browser through which a user may interact with an implementation of the subject matter described herein), or any combination of such back-end, middleware, or front-end components. Client 120 and servers 110, 115 are generally remote from each other and typically interact through the communications network 105. The relationship of the clients 120 and servers 110, 115 arises by virtue of computer programs running on the respective computers and having a client-server relationship to each other. Clients 120 can be any of a variety of computing platforms that include local applications for providing various functionality within the healthcare environment. Example clients 120 include, but are not limited to, desktop computers, laptop computers, tablets, and other computers/devices with touch-screen interfaces. The local applications can be self-contained in that they do not require network connectivity and/or they can interact with one or more of the servers 110, 115 (e.g., a web browser).

A variety of applications can be executed on the various devices and systems within the computing landscape such as electronic health record applications, medical device monitoring, operation, and maintenance applications, scheduling applications, billing applications and the like.

The network 105 can be coupled to one or more data storage systems 125. The data storage systems 125 can include databases providing physical data storage within the healthcare environment or within a dedicated facility. In addition, or in the alternative, the data storage systems 125 can include cloud-based systems providing remote storage of data in, for example, a multi-tenant computing environment. The data storage systems 125 can also comprise non-transitory computer readable media.

Mobile communications devices (MCDs) 130 can also form part of the computing landscape 100. The MCDs 130 can communicate directly via the network 105 and/or they can communicate with the network 105 via an intermediate network such as a cellular data network. Various types of communication protocols can be used by the MCDs 130 including, for example, messaging protocols such as SMS and MMS.

Various types of medical devices 140 can be used as part of the computing landscape 100. For example, the landscape can include comprise various systems/units for delivering fluid (including medication) to a patient. One particular type of medical device 140 is an infusion module 140A. The infusion modules 140A can include various types of infusion pumps including peristaltic infusion pumps, large volume infusion pumps, patient controlled analgesia, and syringe pumps. The infusion modules 140A can be directly coupled to the network 105 and/or they can be coupled to a medical device 140 which is, in turn, coupled to the network 140.

The medical devices 140 can comprise, unless otherwise specified, any type of device or system with a communications interface that characterizes one or more physiological measurements of a patient and/or that characterize treatment of a patient. In some cases, the medical devices 140 communicate via peer to peer wired or wireless communications with another medical device 140 (as opposed to communicating with the network 105). For example, the medical device 140 can comprise a bedside vital signs monitor that is connected to other medical devices 140, namely a wireless pulse oximeter and to a wired blood pressure monitor. One or more operational parameters of the medical devices 140 can be locally controlled by a clinician, controlled via a clinician via the network 105, and/or they can be controlled by one or more of a server 115, 120, a client 125, a MCD 130, and/or another medical device 140.

The computing landscape 100 can provide various types of functionality as may be required within a healthcare environment such as a hospital. For the medical devices 140 can provide data characterizing one or more physiological measurements of a patient and/or treatment of a patient (e.g., medical device 140 can be an infusion management system, etc.). The data generated by the medical devices 140 can be communicated to other medical devices 140, the servers 115, 120, the clients 120, the MCDs 125, and/or stored in the data storage systems 125.

The computing landscape 100 can also include at least one medication ordering system 145 (which can include any variety of feeds that relate to medication orders in a hospital environment). The medication ordering system 145 can be coupled to the network and enable orders (e.g., prescriptions, etc.) to be generated and monitored. The medication order system 145 can be accessed, for example, via the one of the clients 120 and MCDs 130 via the application server 115. The medication ordering system 145 can specify a plurality of medications and/or other fluids to be infused into a patient over a pre-defined period of time and according to a pre-defined sequence via at least one infusion module 140A. These orders can be stored in the data storage 125 and/or pushed out to other clients 120, an MCD 130, and/or one or more of the medical devices 140. In some cases, caregivers alter the timing and sequence of such medication delivery based on reactions from the patient (as measured by various physiological sensors, etc.).

One more of the medical devices 140 (such as infusion modules 140A) can monitor an amount of fluid (e.g., medication, etc.) delivered to a patient. Fluids delivered to patients are referred to herein as infusions. Unless otherwise specified, references herein to medications should also be construed to include non-medication fluids (e.g., blood, saline, etc.) for delivery to a patient via an infusion module 140A.

As noted above, containers housing fluids such as medication often vary from the volumes ordered by a pharmacist/clinician. A software-implemented infusion management platform 150 can be provided that includes a graphical user interface for tracking and monitoring infusions for one or more patients (as will be described in further detail below). The infusion management platform 150 can communicate with the infusion modules 140A via the network 105. The infusion modules 140A can directly or indirectly provide data comprising/characterizing various attributes relating to a particular infusion to the infusion management platform 150 (e.g., patient identifier, medication container identifier, medication type, rate of medication administration, infusion module identifier, etc.). Such attributes can be provided, for example, via messages sent from the infusion modules 140A. In some cases, the infusion management platform 150 receives medication orders from the medication ordering system 145 and then associates such orders with particular infusion modules 140A and/or particular patients (who are later associated with the infusion modules 140A).

Figure 2:
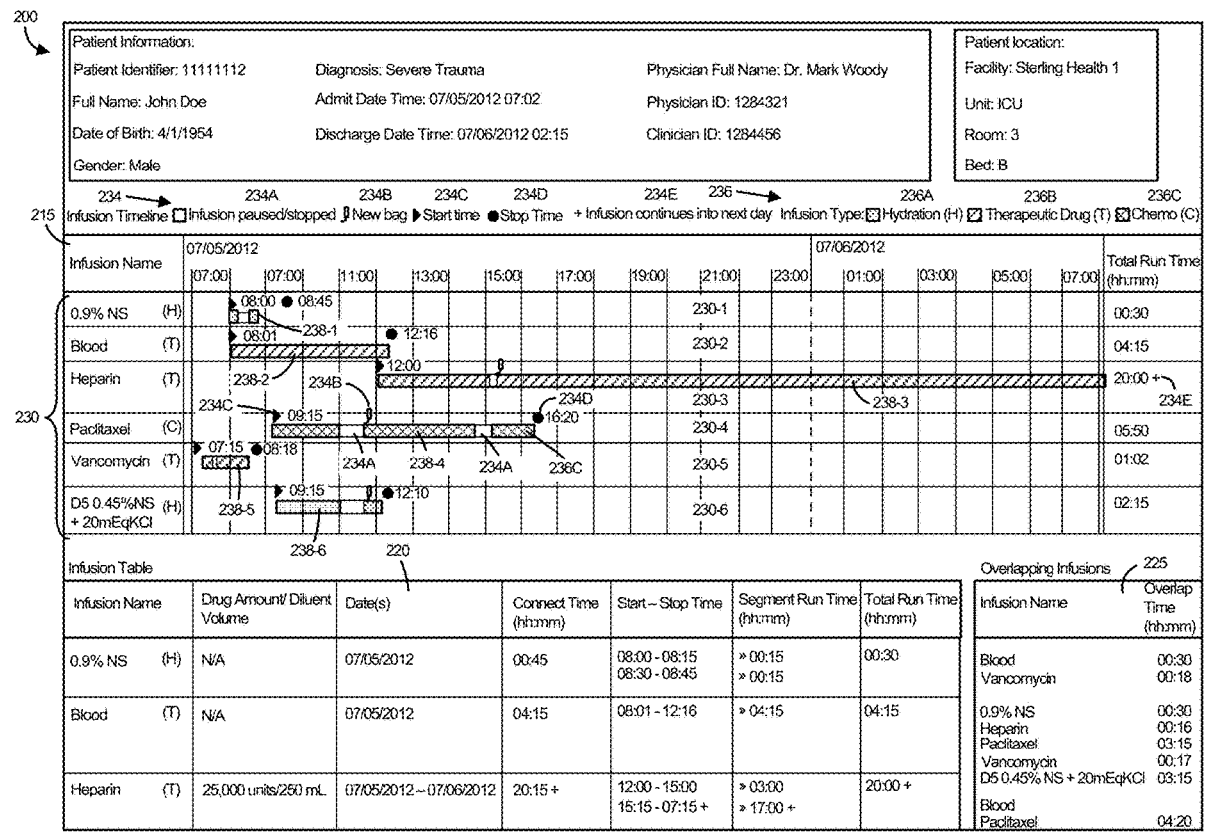
FIG. 2 is a first diagram illustrating a view of a graphical user interface displaying infusion related data over multiple infusion channels.
Figure 3:
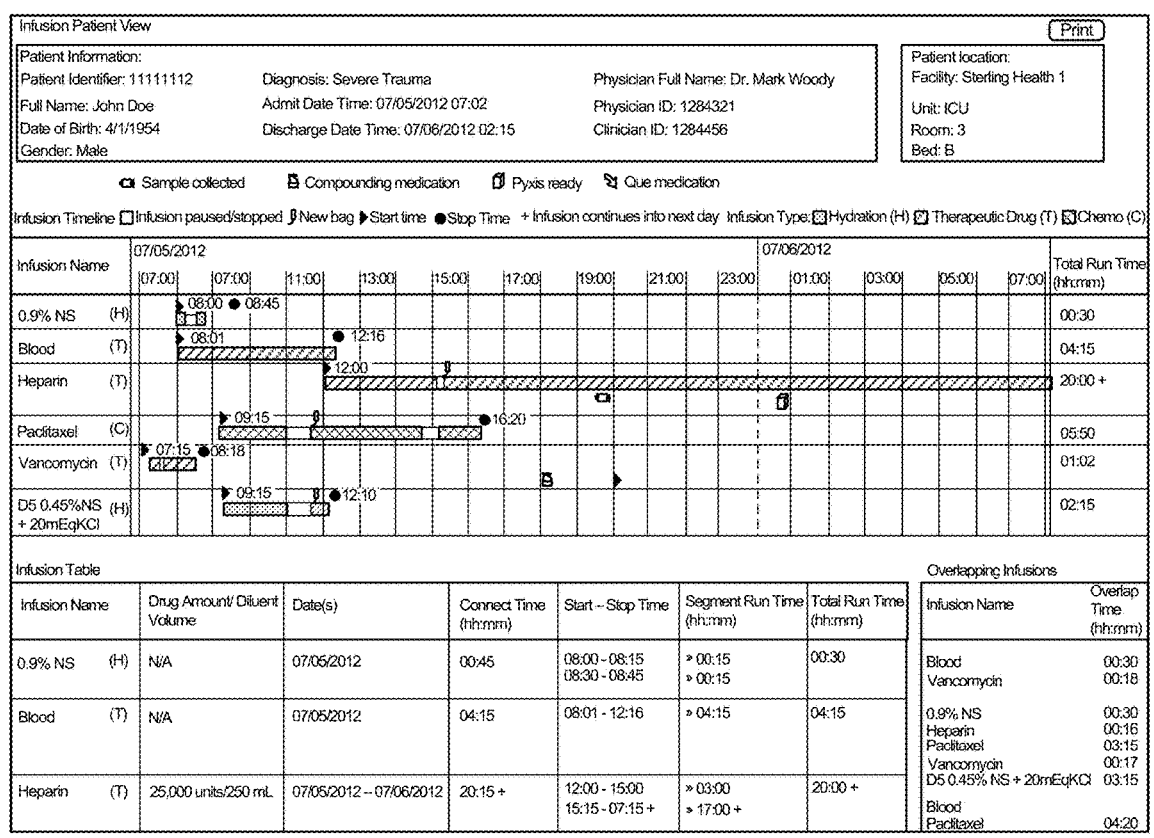
FIG. 3 is a second diagram illustrating a view of a graphical user interface displaying infusion related data over multiple infusion channels.
Figure 4:
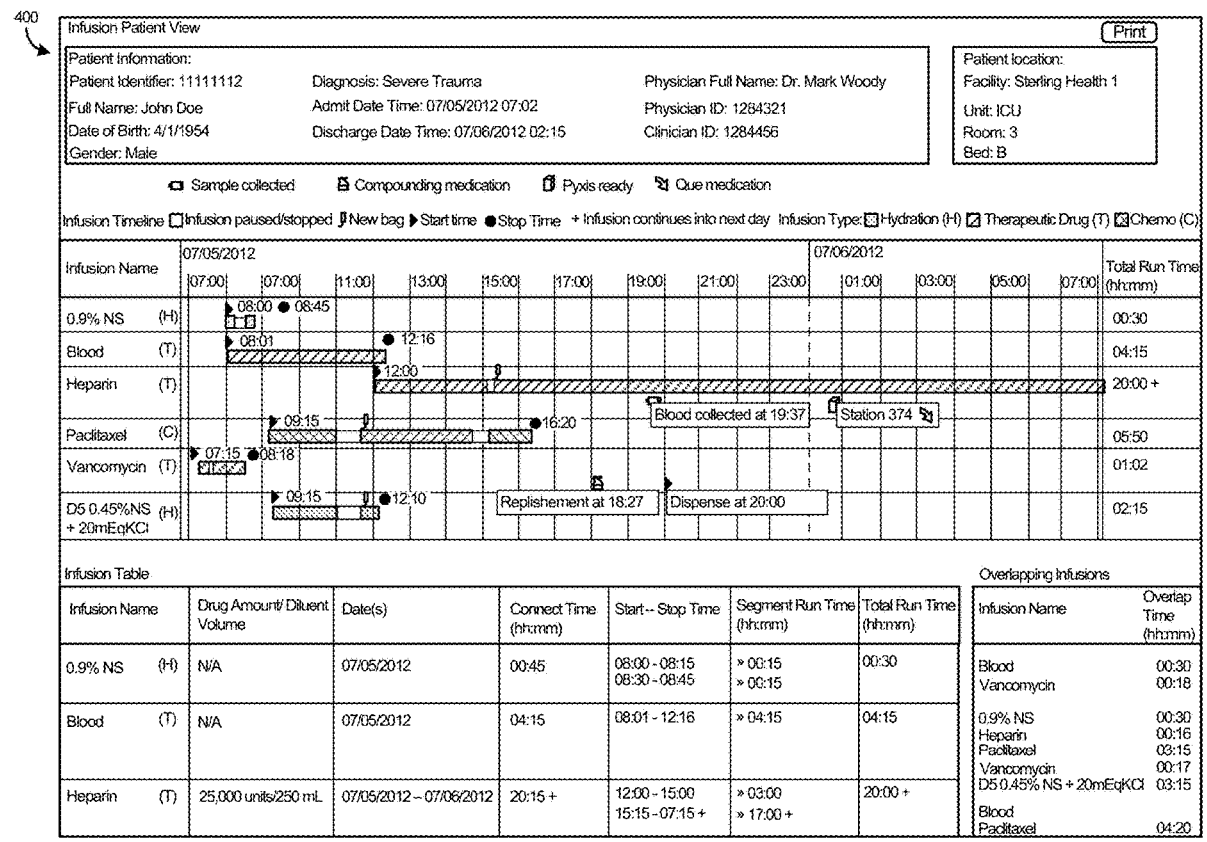
FIG. 4 is a third diagram illustrating a view of a graphical user interface displaying infusion related data over multiple infusion channels.

FIG. 2 is a view 200 of a graphical user interface generated by the infusion management platform 150 that temporally displays infusion data for a patient derived from two or more infusion channels. FIGS. 3 and 4 show alternate views 300, 400 of the graphical user interface generated by the infusion management platform 150. These views are left without specific markings to further illustrate the various aspects of the graphical user interface. With reference to diagram 300 of FIG. 3, the graphical user interface can include a patient information section 205, a patient location section 210, an infusion timeline section 215, an infusion table 220, and overlapping infusions section 225. It will be appreciated that sections 205-225 may be displayed in different positions, in different relative sizes, and/or omitted depending on the desired implementation. The patient information section 205 can provide various information about the patient receiving infusions such as a patient identifier, a diagnosis, a caregiver/physician name (and identifiers for same), data of birth, admission and discharge times. The patient location section 210 can provide information characterizing/identifying a location of the patient. The infusion timeline section 215, as will be described in further detail below, can provide a view of temporal infusion events across multiple infusion channels. The infusion table 220 can provide further details regarding various infusion events including those illustrated in the timeline section 215 as well as any manually administered infusions that are separate from the infusion modules 140A. The overlapping infusions section 225 can group data identifying infusion events that occurred concurrently. Such grouping can be helpful to identify courses of treatment involving multiple infusions (e.g., treatments having multiple infusions that are only reimbursable via a single billing code, etc.).

The infusion timeline section 215 can include a plurality of swim lanes 230 that each display data characterizing infusion events across different infusion channels. While the swim lanes 230 are illustrated as having a horizontal orientation, it will be appreciated that a vertical orientation can be also be implemented. Further, it will be appreciated that the spacing and/or width of the swim lanes can be uniform or they can vary based on, for example, infusion types (with more important infusion types being more prominently displayed). The infusion timeline section 215 can include a time span section 232 with various time demarcations (e.g., two hour intervals, etc.).

The infusion timeline section 215 can include other complementary information relating to the visualizations in the swim lanes including an infusion event key 234 that corresponds certain infusion events with specific visualizations. In one variation, the infusion event key 234 comprises a series of graphical icons 234A-234E that correspond to infusion events such as infusion paused/stopped 234A, new medication container (e.g., IV bag, etc.) 234B, start time 234C, stop time 234D, and infusion continued into the next day 234E.

An infusion type key 236 can be displayed that associates visualizations with types of infusions. In one variation, the infusion type key 236 comprises different color coding for infusion types such as hydration 236A, therapeutic drugs 236B, and chemotherapy 236C.

As illustrated in FIG. 2, within each swim lane 230 there can be bars 238 (which in this example, are horizontally arranged) indicating a time period during which an infusion is administered (using, for example, the time span section 232). It will be appreciated that other types of visualizations can be utilized including dotted lines, continuous elements (e.g., circles, etc.) and the like. Using the third swim lane 230-4 as an example, an infusion of Paclitaxel is initiated at 9:15 via a particular infusion channel as indicated by the beginning of the corresponding bar 238-4. The bar 238-4 can have a graphical icon 234A (in this case a triangular shape) that corresponds to the start time of the infusion and that can be placed immediately above the beginning of bar 238-4. In addition, a time stamp can also be provided above the bar 238-4. The bar 238-4 continues until 11:00 where the visualization indicates (via a graphical icon 234A showing an interruption of the bar 238-4) that Paclitaxel infusion was stopped until 11:45 at which time a new medication container was connected to the infusion channel (and as indicated by the new medication container graphical element 234). The Paclitaxel infusion can then continue (as indicated by the bar 238-4) until 14:45 at which point there was a pause in the infusion (as indicated by the graphical icon 234A above the bar 238-4). The Paclitaxel infusion continues at 15:15 (as indicated by the bar 238-4) until it terminates at 16:20 (as can be indicated by both a stop time graphical icon 234D and by a time stamp). Furthermore, the bar in the swim lane 230-4 can be colored according to the chemotherapy coloring scheme (as indicated by the infusion type key 236 and also be indicated by the parenthetical (C)).

Various aspects of the graphical user interface can permit a user to obtain further information about a particular infusion over a particular channel. For example, in some variations, the graphical user interface can include a series of graphical user interface elements which, which activated, causes complementary information to be displayed in one or more of the patient information section 205, the patient location section 210, the infusion timeline section 215, the infusion table 220, and the overlapping infusions section 225. Activating, in this regard, can include any type of user interaction with such graphical user interface elements including clicking, hovering, and/or various touch-screen interface gestures. For example, by activating a graphical user interface element corresponding to the bar 238-4 in the Paclitaxel swim lane 230-4 additional information can be temporarily displayed on or adjacent to the bar 238-4 that characterizes the infusion and/or data associated with the Paclitaxel infusion can be prominently displayed in one or more of the infusion table section 220 and the overlapping infusions section 225.

The subject matter described herein can be applied to any of a variety of use cases. For example, the current subject matter can provide a timeline view of patient status: orders, labs, administered medication and IV services. Pop up/overlaid elements or other forms of graphical representation involving sequentiality of data can be displayed.

The timeline view can also be used to identify medication order mismatch. The timeline can show where there is a mismatch that may potentially be of concern.

The timeline can show relevant pump parameters (e.g., with a mouse-over) when a point of interest on the timeline is addressed. Pump parameters can be shown at that specific time. In addition, and optionally, a pop up can open to show the values of the same parameter over a wider temporal window to allow a better understanding of the trend of that parameter.

The logistic status of the medication container can be made available. This status indicator can cover the entire process from the order status to the floor location where the medication is available. This status is how the user knows where the next medication is in the process.

The timeline can shows upcoming medication milestones from the medication order in association with the lab milestones.

The timeline can show that lab results are ready and a marker can be dropped on the timeline to show the exact point in time.

The timeline can show lab exceptions that could be potentially dangerous for the patient and that can affect the treatment outcome.

Figure 5:
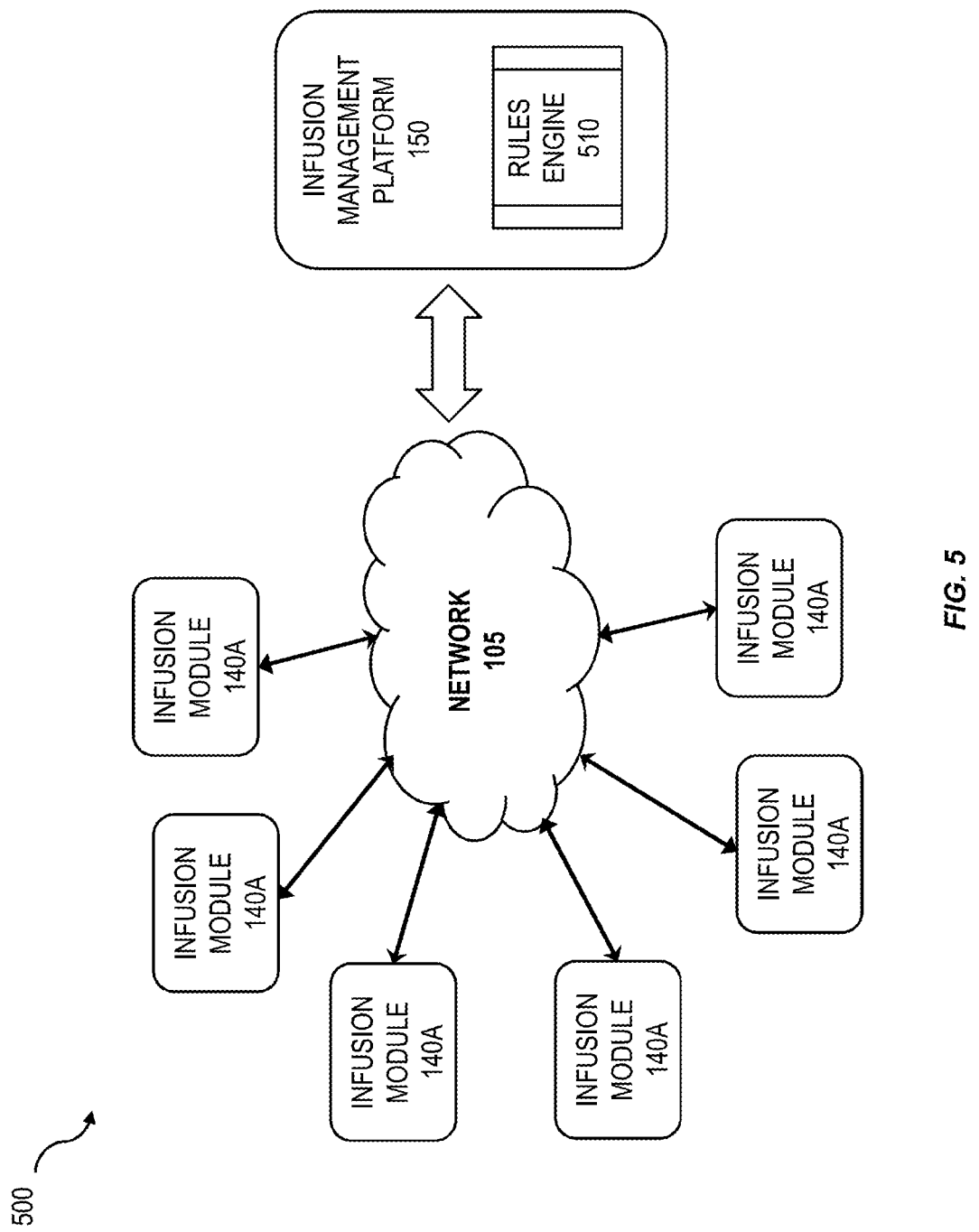
FIG. 5 is a diagram illustrating an aspect of the computing landscape of FIG. 1.

FIG. 5 is a diagram 500 showing a different view of FIG. 1 in which the infusion modules 140A are connected to the infusion management platform 150 (either directly or indirectly as described above) via the network 105. The infusion management platform 150 comprises a rules engine 510 that includes a set of rules (at least some of which are user configurable) that define how the infusion events are identified/characterized from the data generated by the infusion modules 140A and what actions to take in relation to such events. The rules engine 510 can also track and/or maintain the times for identified infusion events so that they can be properly displayed in the graphical user interface at the correct time point. The rules engine 510 can be incorporated into the infusion management platform 150 and/or it can be remote and accessed via a web service by the infusion management platform 150. Various types of rules can be utilized by the rules engine 510 including those described in co-pending application U.S. patent application Ser. No. 13/802,277 filed concurrently herewith and entitled: "Infusion Management Platform for Medication Container Volume Tracking".

Figure 6:
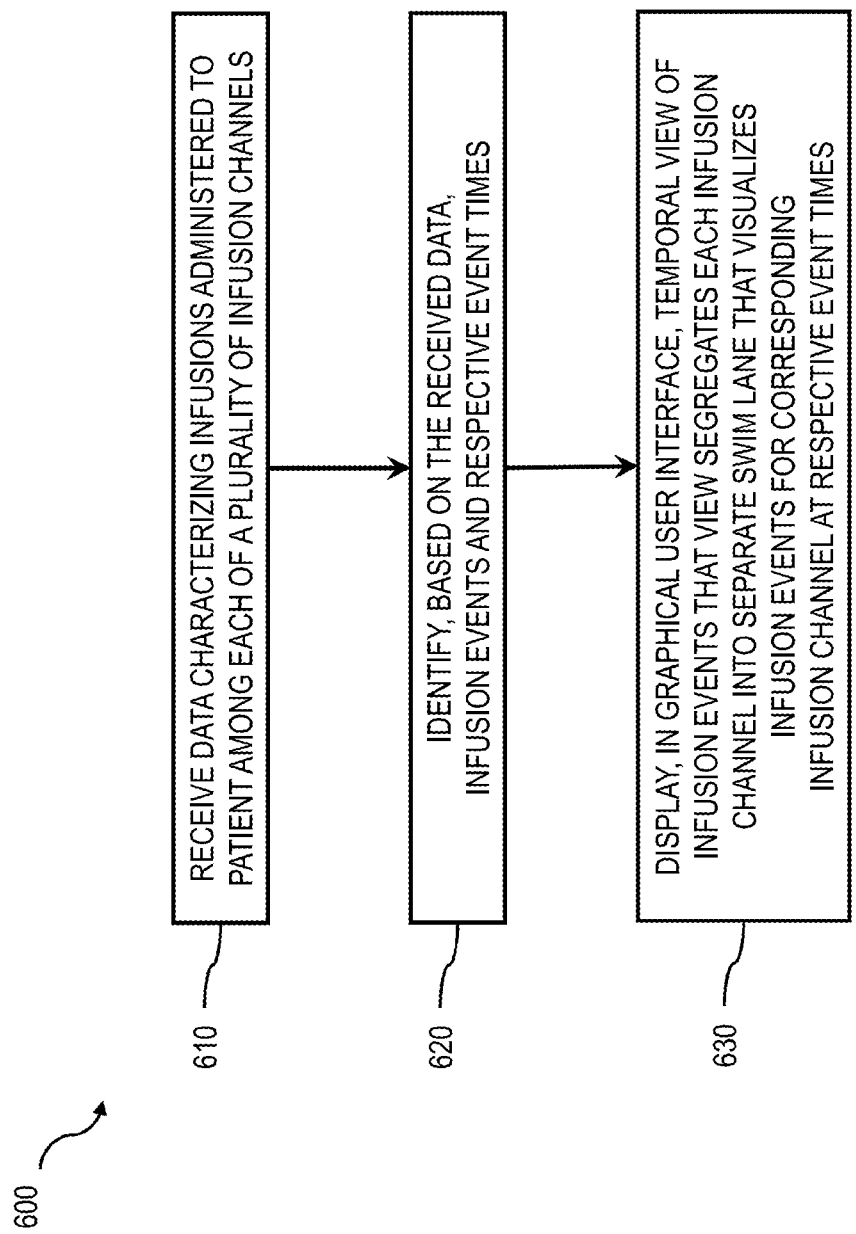
FIG. 6 is a process flow diagram illustrating a method for displaying the infusion related data in the graphical user interface.

FIG. 6 is a process flow diagram 600 in which, at 610, data is received that characterizes infusions administered to a patient among each of a plurality of infusion channels. Thereafter, at 620, a plurality of infusion events and respective event times are identified based on the received data. Subsequently, a temporal view of the infusion events are displayed, at 630, in a graphical user interface. The temporal view segregates each channel into a separate swim lane that each visualize infusion events for the corresponding channel at the respective event times.

It will be appreciated that the data represented in the graphical user interfaces can comprise real-time or near real-time data obtained from an infusion module. In some cases, the data represents historical infusions. In other cases, a combination of real-time/near real-time and historical data can be viewed. Further, future events/predicted events can also be rendered in the graphical user interface.

The current subject matter can also be used to generate reports that comprise one or more aspects rendered in the graphical user interfaces such as the timeline. These reports can be in addition or in lieu of the rendering of the graphical user interface.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitory, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. An infusion management and monitoring system comprising:
   an infusion pump; and a non-transitory computer readable medium comprising instructions executable by a processor to cause a remote device separate from and in communication with the infusion pump to:

receive data for a medication to be administered to a patient via the infusion pump within a healthcare environment, the data for the medication comprising one or more of a medication name, a medication amount to be administered, or date or time data related to when the medication is scheduled to be administered;

receive from the infusion pump data for administration of the medication to the patient, the data for the administration of the medication comprising one or more of a patient identifier, a medication container identifier, a medication type, a rate of medication administration, an infusion pump identifier, or one or more infusion events and respective event times;

determine a status of the administration of the medication based on at least one of the data for the medication or the data for the administration of the medication; and transmit the status to a mobile communication device within the healthcare environment, the transmitting causing the mobile communication device to: provide, on a graphical user interface, information about the administration of the medication, wherein the information is a timeline of the infusion events and the respective event times; and provide, on the graphical user interface and in response to a user interaction with the information, parameters characterizing operation of the infusion pump.

2. The infusion management and monitoring system of claim 1, wherein the instructions executable by the processor further cause the remote device to:

receive the data for the medication from a medication ordering system in communication with the remote device.

3. The infusion management and monitoring system of claim 2, wherein the instructions executable by the processor further cause the remote device to:

associate a medication order comprising the data for the medication with the infusion pump and with the patient based at least in part on an association between the patient the infusion pump.

4. The infusion management and monitoring system of claim 1, wherein the status indicates progress of the administration of the medication.

5. The infusion management and monitoring system of claim 1, wherein the status indicates whether the infusion pump is administering the medication.

6. The infusion management and monitoring system of claim 1, wherein the one or more infusion events comprise infusion paused, infusion stopped, new medication container, administration start time, administration stop time, or infusion continued into subsequent day.

7. The infusion management and monitoring system of claim 1, wherein the instructions executable by the processor further cause the remote device to:

provide, on the graphical user interface, at least two data about the administration of the medication.

8. The infusion management and monitoring system of claim 1, wherein the instructions executable by the processor further cause the remote device to:

provide, on the graphical user interface, a patient information section, a patient location section, a table including information regarding infusion status, or an overlapping infusions section.

9. The infusion management and monitoring system of claim 1, wherein the instructions executable by the processor further cause the remote device to:

provide, on the graphical user interface and in response to the user interaction, a view of complementary information, the complementary information related to the information provided on the graphical user interface.

10. The infusion management and monitoring system of claim 1, wherein the user interaction comprises selection of a particular time in the timeline.

11. The infusion management and monitoring system of claim 10, wherein the instructions executable by the processor further cause the remote device to display the parameters characterizing operation of the infusion pump for the particular time selected in the timeline.

12. The infusion management and monitoring system of claim 1, wherein the instructions executable by the processor further cause the remote device to display, on the mobile communication device, the status of the administration of the medication.

13. The infusion management and monitoring system of claim 1, wherein the instructions executable by the processor further cause the remote device to associate the status of the administration of the medication in a record associated with the patient.

14. The infusion management and monitoring system of claim 13, wherein the record comprises the data for the medication or data of the infusion pump.

15. The infusion management and monitoring system of claim 1, wherein information is from a plurality of infusion pumps, the plurality of infusion pumps including the infusion pump.

16. The infusion management and monitoring system of claim 15, wherein the instructions executable by the processor further cause the remote device to:

display, based on selection of the infusion pump from the plurality of infusion pumps, the parameters characterizing operation of the infusion pump.

17. The infusion management and monitoring system of claim 1, wherein information is from a plurality of data sources, the plurality of data sources including the infusion pump.

18. The infusion management and monitoring system of claim 17, wherein the instructions executable by the processor further cause the remote device to:

display, based on selection of the infusion pump from the plurality of data sources, the parameters characterizing operation of the infusion pump.

19. A non-transitory computer readable medium comprising instructions executable by a processor to cause a remote device separate from and in communication with an infusion pump to:

receive data for a medication to be administered to a patient via the infusion pump within a healthcare environment, the data for the medication comprising one or more of a medication name, a medication amount to be administered, or date or time data related to when the medication is scheduled to be administered;

receive from the infusion pump data for administration of the medication to the patient, the data for the administration of the medication comprising one or more of a patient identifier, a medication container identifier, a medication type, a rate of medication administration, an infusion pump identifier, or one or more infusion events and respective event times;

determine a status of the administration of the medication based on at least one of the data for the medication or the data for the administration of the medication; and transmit the status to a mobile communication device within the healthcare environment, the transmitting causing the mobile communication device to: provide, on a graphical user interface, information about the administration of the medication, wherein the information is a timeline of the infusion events and the respective event times; and provide, on the graphical user interface and in response to a user interaction, parameters characterizing operation of the infusion pump.

20. The non-transitory computer readable medium of claim 19, wherein the instructions executable by the processor further cause the remote device to:

receive the data for the medication from a medication ordering system in communication with the remote device.

21. The non-transitory computer readable medium of claim 20, wherein the instructions executable by the processor further cause the remote device to:

associate a medication order comprising the data for the medication with the infusion pump and with the patient based at least in part on an association between the patient the infusion pump.

22. The non-transitory computer readable medium of claim 19, wherein the status indicates progress of the administration of the medication.

23. The non-transitory computer readable medium of claim 19, wherein the status indicates whether the infusion pump is administering the medication.

24. The non-transitory computer readable medium of claim 19, wherein the one or more infusion events comprise infusion paused, infusion stopped, new medication container, administration start time, administration stop time, or infusion continued into subsequent day.

25. The non-transitory computer readable medium of claim 19, wherein the instructions executable by the processor further cause the remote device to:

provide, on the graphical user interface, a patient information section, a patient location section, a table including information regarding infusion status, or an overlapping infusions section.

26. The non-transitory computer readable medium of claim 19, wherein the instructions executable by the processor further cause the remote device to:

provide, on the graphical user interface and in response to the user interaction, a view of complementary information, the complementary information related to the information provided on the graphical user interface.

27. The non-transitory computer readable medium of claim 19, wherein the user interaction comprises selection of a particular time in the timeline.

28. The non-transitory computer readable medium of claim 27, wherein the instructions executable by the processor further cause the remote device to display the parameters characterizing operation of the infusion pump for the particular time selected in the timeline.

29. The non-transitory computer readable medium of claim 19, wherein the instructions executable by the processor further cause the remote device to display, on the mobile communication device, the status of the administration of the medication.

30. The non-transitory computer readable medium of claim 19, wherein the instructions executable by the processor further cause the remote device to associate the status of the administration of the medication in a record associated with the patient.

* * * * *